US012655074B2

(12) United States Patent
Aasberg-Petersen et al.

(10) Patent No.: US 12,655,074 B2
(45) Date of Patent: Jun. 16, 2026

(54) SYNTHESIS GAS PRODUCTION FROM CO₂ AND STEAM FOR SYNTHESIS OF FUELS

(71) Applicant: TOPSOE A/S, Kgs. Lyngby (DK)

(72) Inventors: Kim Aasberg-Petersen, Allerød (DK); Peter Mølgaard Mortensen, Roskilde (DK)

(73) Assignee: TOPSOE A/S, Kgs. Lyngby (DK)

( * ) Notice: Subject to any disclaimer, the term of this patent is extended or adjusted under 35 U.S.C. 154(b) by 506 days.

(21) Appl. No.: 18/257,339

(22) PCT Filed: Jan. 19, 2022

(86) PCT No.: PCT/EP2022/051090
§ 371 (c)(1),
(2) Date: Jun. 14, 2023

(87) PCT Pub. No.: WO2022/161823
PCT Pub. Date: Aug. 4, 2022

(65) Prior Publication Data
US 2024/0025818 A1     Jan. 25, 2024

(30) Foreign Application Priority Data

Jan. 27, 2021    (EP) ..................................... 21153815
Jul. 15, 2021    (EP) ..................................... 21185834

(51) Int. Cl.
*C07C 1/04*         (2006.01)
*C01B 3/12*         (2006.01)
(Continued)

(52) U.S. Cl.
CPC .............. *C07C 1/0485* (2013.01); *C01B 3/12* (2013.01); *C01B 3/384* (2013.01); *C07C 1/041* (2013.01);
(Continued)

(58) Field of Classification Search
CPC .. C10G 2/34; C10G 2400/04; C10G 2400/08; C01B 3/12; C01B 3/384;
(Continued)

(56) References Cited

U.S. PATENT DOCUMENTS

| | | | |
|---|---|---|---|
| 3,499,947 A | 3/1970 | Johnson | |
| 3,763,205 A | 10/1973 | Green | |

(Continued)

FOREIGN PATENT DOCUMENTS

| | | |
|---|---|---|
| AU | 70674/81 A | 11/1981 |
| AU | 2019275850 A1 | 11/2020 |

(Continued)

OTHER PUBLICATIONS

International Search Report and Written Opinion received for PCT Patent Application No. PCT/EP2021/085707, mailed on Mar. 14, 2022, 12 pages.

(Continued)

*Primary Examiner* — Jafar F Parsa
(74) *Attorney, Agent, or Firm* — Boone IP Law

(57) ABSTRACT

A system is described for providing a hydrocarbon product stream. An electrolysis section provides a syngas stream from a first feed comprising CO₂ and a second feed comprising H₂O, which is then passed to an F-T section where it is converted to a hydrocarbon product stream and a tail gas stream. An electrical steam reformer section said tail gas stream and convert it to a second syngas stream, which is then recycled upstream the FT section. A process is also provided for converting a first feed comprising CO₂ and a second feed comprising H₂O to a first hydrocarbon product stream in a system according to the invention. The system of the invention can be combined with an upgrading section, in a gas-to-liquid plant.

20 Claims, 2 Drawing Sheets

100

Figure 1:
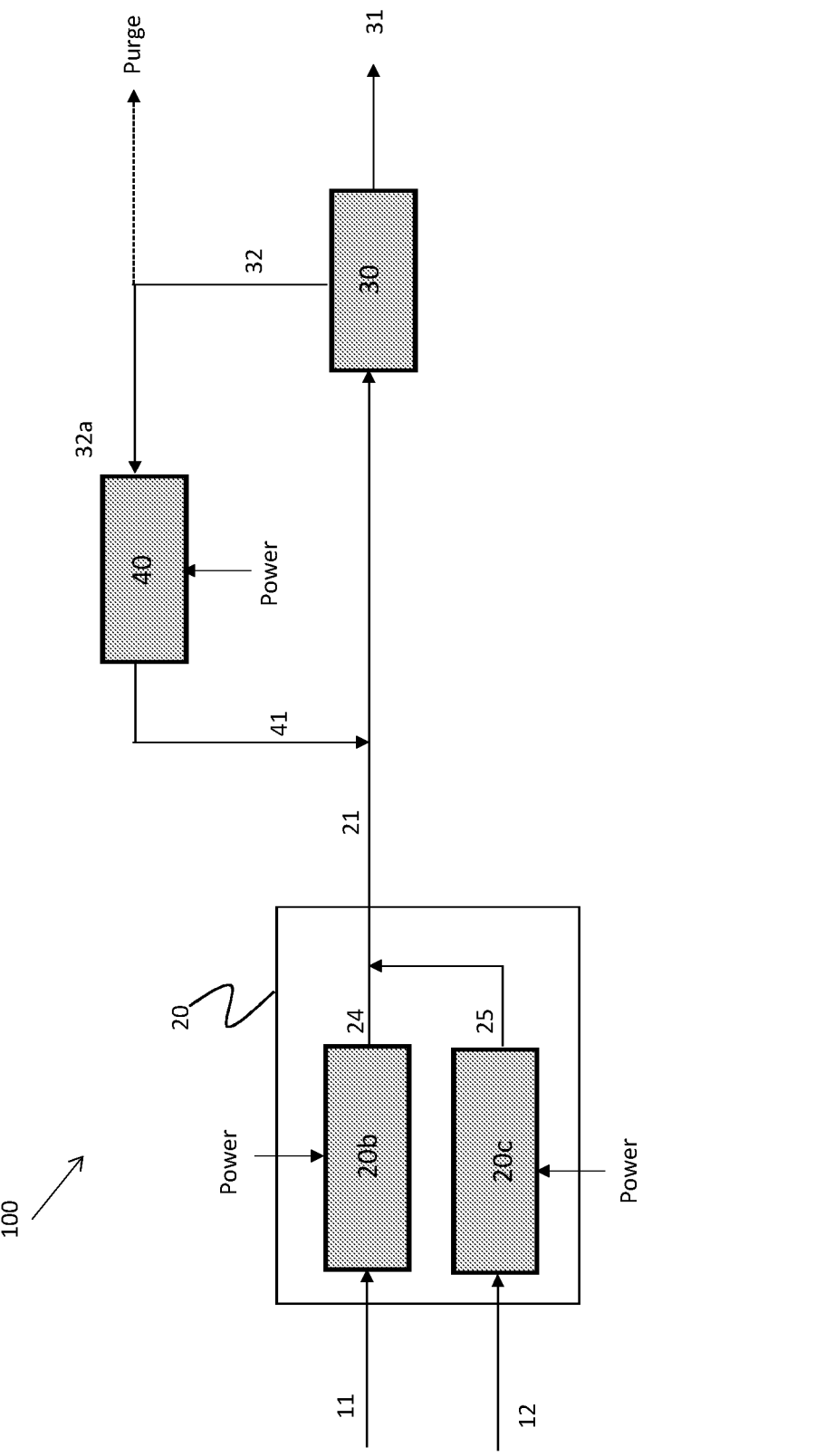

(51) Int. Cl.

| | |
|---|---|
| *C01B 3/384* | (2026.01) |
| *C10G 2/00* | (2006.01) |
| *C25B 1/23* | (2021.01) |
| *C25B 9/19* | (2021.01) |
| *C25B 13/05* | (2021.01) |
| *C25B 13/08* | (2006.01) |

(52) U.S. Cl.
CPC .................. *C10G 2/34* (2013.01); *C25B 1/23* (2021.01); *C25B 9/19* (2021.01); *C25B 13/05* (2021.01); *C25B 13/08* (2013.01); *C01B 2203/0233* (2013.01); *C01B 2203/0283* (2013.01); *C01B 2203/062* (2013.01); *C01B 2203/085* (2013.01); *C01B 2203/148* (2013.01); *C10G 2400/04* (2013.01); *C10G 2400/08* (2013.01)

(58) Field of Classification Search
CPC .... C01B 2203/0233; C01B 2203/0283; C01B 2203/062; C01B 2203/148; C25B 1/23; C25B 9/19; C25B 13/05; C25B 13/08
See application file for complete search history.

(56) References Cited

U.S. PATENT DOCUMENTS

| | | | |
|---|---|---|---|
| 3,871,993 | A | 3/1975 | Morrison |
| 4,157,356 | A | 6/1979 | Bulford |
| 4,520,216 | A | 5/1985 | Skov et al. |
| 4,520,224 | A | 5/1985 | Kamimura et al. |
| 4,910,228 | A | 3/1990 | Lywood |
| 5,128,003 | A | 7/1992 | Murdoch et al. |
| 5,202,547 | A | 4/1993 | Abe et al. |
| 5,296,198 | A | 3/1994 | Abe et al. |
| 5,321,191 | A | 6/1994 | Alagy et al. |
| 5,631,302 | A | 5/1997 | Koenig et al. |
| 5,817,286 | A | 10/1998 | Martin et al. |
| 5,827,901 | A | 10/1998 | Koenig et al. |
| 5,976,723 | A | 11/1999 | Boffito et al. |
| 6,207,042 | B1 | 3/2001 | Holtermann |
| 6,322,757 | B1 | 11/2001 | Cohn et al. |
| 6,433,029 | B1 | 8/2002 | Fitzpatrick |
| 6,696,501 | B2 | 2/2004 | Schanke |
| 6,746,650 | B1 | 6/2004 | Lesieur |
| 7,960,441 | B2 | 6/2011 | Wolf |
| 8,568,581 | B2 | 10/2013 | Sivasankar et al. |
| 9,067,847 | B2 | 6/2015 | Bashir et al. |
| 9,101,890 | B2 | 8/2015 | Tonkovich et al. |
| 9,238,598 | B2 | 1/2016 | Hammad et al. |
| 9,752,080 | B2 | 9/2017 | Christensen et al. |
| 10,011,789 | B2 | 7/2018 | De Klerk |
| 10,596,544 | B2 | 3/2020 | Motoshige et al. |
| 11,214,488 | B2 | 1/2022 | Rueger |
| 12,246,298 | B2 | 3/2025 | Mortensen et al. |
| 2002/0051741 | A1 | 5/2002 | Abe et al. |
| 2002/0081253 | A1 | 6/2002 | Abe |
| 2002/0094312 | A1 | 7/2002 | Hanus et al. |
| 2002/0119084 | A1 | 8/2002 | Boneberg et al. |
| 2003/0065042 | A1 | 4/2003 | Shaw |
| 2003/0094381 | A1 | 5/2003 | Bors et al. |
| 2003/0143135 | A1 | 7/2003 | O'Rear et al. |
| 2003/0191199 | A1 | 10/2003 | O'Rear |
| 2004/0016650 | A1 | 1/2004 | Klug |
| 2004/0081875 | A1 | 4/2004 | Milliken et al. |
| 2004/0197246 | A1 | 10/2004 | Stevens et al. |
| 2004/0265225 | A1 | 12/2004 | Watson et al. |
| 2005/0069485 | A1 | 3/2005 | Jung et al. |
| 2006/0116543 | A1 | 6/2006 | Bellet et al. |
| 2006/0124445 | A1 | 6/2006 | Labrecque et al. |
| 2006/0254141 | A1 | 11/2006 | Krause et al. |
| 2007/0045125 | A1 | 3/2007 | Hartvigsen et al. |
| 2007/0244208 | A1 | 10/2007 | Shulenberger et al. |
| 2008/0021251 | A1 | 1/2008 | Iaccino et al. |
| 2008/0023338 | A1 | 1/2008 | Stoots et al. |
| 2008/0081844 | A1 | 4/2008 | Shires et al. |
| 2008/0096985 | A1 | 4/2008 | Minta et al. |
| 2008/0169449 | A1 | 7/2008 | Mundschau |
| 2008/0224097 | A1 | 9/2008 | Fujie et al. |
| 2009/0220390 | A1 | 9/2009 | Grouset et al. |
| 2009/0235587 | A1 | 9/2009 | Hawkes et al. |
| 2009/0252919 | A1 | 10/2009 | Ogura |
| 2009/0289227 | A1 | 11/2009 | Rising |
| 2009/0307975 | A1 | 12/2009 | Wolf |
| 2010/0111781 | A1 | 5/2010 | Takahashi et al. |
| 2010/0186291 | A1 | 7/2010 | Yie et al. |
| 2010/0296984 | A1 | 11/2010 | Ando et al. |
| 2011/0020207 | A1 | 1/2011 | Siegert |
| 2011/0136027 | A1 | 6/2011 | Chen et al. |
| 2011/0253550 | A1 | 10/2011 | Hoffmann |
| 2011/0253551 | A1 | 10/2011 | Lane et al. |
| 2011/0293510 | A1 | 12/2011 | Grannell et al. |
| 2012/0095268 | A1 | 4/2012 | Tonkovich et al. |
| 2012/0178951 | A1 | 7/2012 | Krull et al. |
| 2012/0201717 | A1 | 8/2012 | Singh et al. |
| 2012/0228150 | A1 | 9/2012 | Kang et al. |
| 2012/0288776 | A1 | 11/2012 | Nagaosa |
| 2012/0326090 | A1 | 12/2012 | Han et al. |
| 2013/0034478 | A1 | 2/2013 | Doty |
| 2013/0041051 | A1 | 2/2013 | Zuberbuhler et al. |
| 2013/0065974 | A1 | 3/2013 | Kresnyak |
| 2013/0082211 | A1 | 4/2013 | Aasberg-Petersen et al. |
| 2013/0345326 | A1 | 12/2013 | Bashir et al. |
| 2014/0194539 | A1 | 7/2014 | Hammad et al. |
| 2014/0272734 | A1 | 9/2014 | Braun et al. |
| 2014/0291162 | A1 | 10/2014 | Sala et al. |
| 2014/0326640 | A1 | 11/2014 | De Klerk |
| 2015/0129805 | A1 | 5/2015 | Karpenko et al. |
| 2015/0175509 | A1 | 6/2015 | Almqvist et al. |
| 2015/0259202 | A1 | 9/2015 | Dybkjr et al. |
| 2015/0299871 | A1 | 10/2015 | Chen et al. |
| 2015/0321918 | A1 | 11/2015 | Noyes |
| 2015/0337211 | A1 | 11/2015 | Dahl |
| 2016/0002036 | A1 | 1/2016 | Kolaczkowski et al. |
| 2016/0024391 | A1 | 1/2016 | Christensen et al. |
| 2016/0045841 | A1 | 2/2016 | Kaplan et al. |
| 2016/0168489 | A1 | 6/2016 | Kwon et al. |
| 2016/0319381 | A1 | 11/2016 | Achatz et al. |
| 2016/0355932 | A1 | 12/2016 | Reytier et al. |
| 2017/0106360 | A1 | 4/2017 | Meriam |
| 2018/0066371 | A1 | 3/2018 | Hong et al. |
| 2018/0127668 | A1 | 5/2018 | Masel |
| 2018/0194632 | A1 | 7/2018 | Jakobsson et al. |
| 2019/0085250 | A1 | 3/2019 | Anzelmo et al. |
| 2019/0112187 | A1 | 4/2019 | Mortensen et al. |
| 2019/0144376 | A1 | 5/2019 | Højlund et al. |
| 2019/0211269 | A1 | 7/2019 | Galloway |
| 2019/0225489 | A1 | 7/2019 | Herskowitz et al. |
| 2019/0249094 | A1 | 8/2019 | Snell et al. |
| 2019/0359894 | A1 | 11/2019 | Heidel et al. |
| 2020/0011225 | A1 | 1/2020 | Hirth et al. |
| 2020/0063273 | A1 | 2/2020 | Masel |
| 2020/0095124 | A1 | 3/2020 | Rueger |
| 2020/0109051 | A1 | 4/2020 | Aasberg-Petersen et al. |
| 2020/0156953 | A1 | 5/2020 | Han |
| 2020/0354216 | A1 | 11/2020 | Mortensen |
| 2021/0054510 | A1 | 2/2021 | Schjødt et al. |
| 2021/0079535 | A1 | 3/2021 | Schjødt et al. |
| 2021/0113983 | A1 | 4/2021 | Mortensen et al. |
| 2021/0171344 | A1 | 6/2021 | Mortensen et al. |
| 2021/0238035 | A1 | 8/2021 | Mortensen et al. |
| 2021/0292925 | A1 | 9/2021 | Mikoshiba et al. |
| 2021/0363079 | A1 | 11/2021 | Pedersen et al. |
| 2022/0081289 | A1 | 3/2022 | De Sarkar et al. |
| 2022/0081291 | A1 | 3/2022 | Mortensen |
| 2022/0081292 | A1 | 3/2022 | De Sarkar et al. |
| 2022/0119255 | A1 | 4/2022 | Mortensen |
| 2022/0162067 | A1 | 5/2022 | Mortensen et al. |

FOREIGN PATENT DOCUMENTS

| | | | |
|---|---|---|---|
| CA | 287219 | A | 2/1929 |
| CA | 2427464 | A1 | 4/1999 |
| CA | 2872194 | A1 | 3/2016 |

(56) References Cited

FOREIGN PATENT DOCUMENTS

| | | | |
|---|---|---|---|
| CL | 200101295 | | 2/2002 |
| CL | 200202268 | | 12/2003 |
| CN | 1031391 | C | 3/1996 |
| CN | 1407959 | A | 4/2003 |
| CN | 1483133 | A | 3/2004 |
| CN | 1774291 | A | 5/2006 |
| CN | 101157563 | A | 4/2008 |
| CN | 101177239 | A | 5/2008 |
| CN | 104169210 | A | 11/2014 |
| CN | 105188903 | A | 12/2015 |
| CN | 109964011 | A | 7/2019 |
| CN | 111247091 | A | 6/2020 |
| CN | 112203757 | A | 1/2021 |
| CN | 112236223 | A | 1/2021 |
| DE | 10104601 | A1 | 8/2002 |
| DE | 102005046746 | A1 | 4/2007 |
| DE | 102010027474 | A1 | 1/2012 |
| DE | 102013102969 | A1 | 9/2014 |
| DE | 102013226126 | A1 | 6/2015 |
| DE | 102015110120 | A1 | 12/2016 |
| EP | 0025205 | A1 | 3/1981 |
| EP | 0502731 | A1 | 9/1992 |
| EP | 0913357 | A1 | 5/1999 |
| EP | 2491998 | A1 | 8/2012 |
| EP | 2594527 | A1 | 5/2013 |
| EP | 2955158 | A1 | 12/2015 |
| EP | 3249027 | A1 | 11/2017 |
| EP | 2874738 | B1 | 9/2018 |
| EP | 3415661 | A1 | 12/2018 |
| EP | 3472370 | A1 | 4/2019 |
| EP | 3574991 | A1 | 12/2019 |
| EP | 3670443 | A1 | 6/2020 |
| GB | 0722025 | A | 1/1955 |
| GB | 0915444 | A | 1/1963 |
| GB | 1269311 | A | 4/1972 |
| GB | 1338352 | A | 11/1973 |
| GB | 1443735 | A | 7/1976 |
| GB | 2077613 | A | 12/1981 |
| GB | 2358148 | A | 7/2001 |
| IT | 20100115 | A1 | 4/2012 |
| JP | 39-028629 | B | 12/1964 |
| JP | 52-018485 | A | 2/1977 |
| JP | 05-006120 | U | 1/1993 |
| JP | 05-222379 | A | 8/1993 |
| JP | 11-130405 | A | 5/1999 |
| JP | 2002-201002 | A | 7/2002 |
| JP | 2003-504485 | A | 2/2003 |
| JP | 2003-226657 | A | 8/2003 |
| JP | 2003-320254 | A | 11/2003 |
| JP | 2008-001584 | A | 1/2008 |
| JP | 2010-195642 | A | 9/2010 |
| JP | 2013-505125 | A | 2/2013 |
| JP | 2014-111768 | A | 6/2014 |
| JP | 2014-152219 | A | 8/2014 |
| JP | 2015-509905 | A | 4/2015 |
| JP | 2016511296 | A | 4/2016 |
| JP | 2018-104282 | A | 7/2018 |
| JP | 2019-514825 | A | 6/2019 |
| JP | 2019-514901 | A | 6/2019 |
| JP | 2019-162612 | A | 9/2019 |
| JP | 2021-525697 | A | 9/2021 |
| KR | 10-2005-0030492 | A | 3/2005 |
| KR | 10-2009-0045519 | A | 5/2009 |
| KR | 10-2009-0068427 | A | 6/2009 |
| KR | 10-2014-0140562 | A | 12/2014 |
| KR | 10-2018-0075285 | A | 7/2018 |
| KR | 10-2019-0080354 | A | 7/2019 |
| TW | 512132 | B | 12/2002 |
| WO | 99/19277 | A1 | 4/1999 |
| WO | 00/01613 | A1 | 1/2000 |
| WO | 00/76651 | A1 | 12/2000 |
| WO | 2004/091773 | A1 | 10/2004 |
| WO | 2007/019801 | A1 | 2/2007 |
| WO | 2007/048641 | A2 | 5/2007 |
| WO | 2007/088923 | A1 | 8/2007 |
| WO | 2007/108014 | A1 | 9/2007 |
| WO | 2009/126765 | A2 | 10/2009 |
| WO | 2010/004300 | A1 | 1/2010 |
| WO | 2010/090863 | A2 | 8/2010 |
| WO | 2011/134705 | A1 | 11/2011 |
| WO | 2012/084609 | A1 | 6/2012 |
| WO | 2012077198 | A1 | 6/2012 |
| WO | 2013/131778 | A2 | 9/2013 |
| WO | 2013/189791 | A1 | 12/2013 |
| WO | 2014/056535 | A1 | 4/2014 |
| WO | 2014/057013 | A1 | 4/2014 |
| WO | 2014/096226 | A1 | 6/2014 |
| WO | 2014/099567 | A1 | 6/2014 |
| WO | 2014/154253 | A1 | 10/2014 |
| WO | 2014/154691 | A1 | 10/2014 |
| WO | 2014170200 | A1 | 10/2014 |
| WO | 2014/180888 | A1 | 11/2014 |
| WO | 2015/014527 | A1 | 2/2015 |
| WO | 2015/015433 | A1 | 2/2015 |
| WO | 2015/123395 | A1 | 8/2015 |
| WO | 2015/128395 | A1 | 9/2015 |
| WO | 2016/091636 | A1 | 6/2016 |
| WO | 2016/207342 | A1 | 12/2016 |
| WO | 2017/014635 | A1 | 1/2017 |
| WO | 2017/036794 | A1 | 3/2017 |
| WO | 2017/186612 | A1 | 11/2017 |
| WO | 2017/186615 | A1 | 11/2017 |
| WO | 2018/153625 | A1 | 8/2018 |
| WO | 2018/206235 | A1 | 11/2018 |
| WO | 2018/228723 | A1 | 12/2018 |
| WO | 2019/020378 | A1 | 1/2019 |
| WO | 2019/020513 | A1 | 1/2019 |
| WO | 2019/020519 | A1 | 1/2019 |
| WO | 2019/104375 | A1 | 6/2019 |
| WO | 2019/110265 | A1 | 6/2019 |
| WO | 2019/110266 | A1 | 6/2019 |
| WO | 2019/110268 | A1 | 6/2019 |
| WO | 2019/110269 | A1 | 6/2019 |
| WO | 2019110267 | A1 | 6/2019 |
| WO | 2019/228795 | A1 | 12/2019 |
| WO | 2019/228796 | A1 | 12/2019 |
| WO | 2019/228797 | A1 | 12/2019 |
| WO | 2019/228798 | A1 | 12/2019 |
| WO | 2020/008008 | A1 | 1/2020 |
| WO | 2020/035574 | A1 | 2/2020 |
| WO | 2020/058859 | A1 | 3/2020 |
| WO | 2020/118236 | A1 | 6/2020 |
| WO | 2020/206538 | A1 | 10/2020 |
| WO | 2020/207926 | A1 | 10/2020 |
| WO | 2020/208008 | A1 | 10/2020 |
| WO | 2020/254121 | A1 | 12/2020 |
| WO | 2021/110754 | A1 | 6/2021 |
| WO | 2021110806 | A1 | 6/2021 |
| WO | 2021/220667 | A1 | 11/2021 |
| WO | 2022/079010 | A1 | 4/2022 |
| WO | 2022/079098 | A1 | 4/2022 |
| WO | 2022079002 | A1 | 4/2022 |
| WO | 2022/136374 | A1 | 6/2022 |
| WO | 2022161823 | A1 | 8/2022 |
| WO | 2022/226230 | A1 | 10/2022 |

OTHER PUBLICATIONS

International Search Report and Written Opinion received for PCT Patent Application No. PCT/EP2021/086678, mailed on Mar. 14, 2022, 11 pages.

International Search Report and Written Opinion received for PCT Patent Application No. PCT/EP2021/086999, mailed on Apr. 7, 2022, 15 pages.

International Search Report and Written Opinion received for PCT Patent Application No. PCT/EP2023/062128, mailed on Sep. 1, 2023, 10 pages.

International Search Report and Written Opinion received for PCT Patent Application No. PCT/EP2023/062129, mailed on Sep. 1, 2023, 10 pages.

Introduction to Energy Chemistry, Dong Guanghua, etc., p. 124, Xuzhouo: China University of Mining and Technology Press, Sep. 2018.

(56)                    References Cited

OTHER PUBLICATIONS

Keim, W., "Synthesis Gas Feedstock for Chemicals", American Chemical Society, Jan. 1, 1987, vol. 25, No. 10, pp. 1-16. (16 pages).

Kongas, Rainer, "Review-Electrochemical CO2 Reduction for CO Production: Comparison of Low- and High-Temperature Electrolysis Technologies", Journal of the Electrochemical Society, Feb. 14, 2020, 167:0044508. (12 pages).

Notice of Allowance received for Chinese Patent Application No. 201980036811, mailed on May 2, 2025, 4 (2 pages of English Translation and 2 pages of Original Document).

Notification to grant right for invention received for Chinese Patent Application No. 202080067396.5, mailed on Sep. 26, 2024, 03 pages (02 pages of English Translation and 01 pages of Original Document).

Office Action received for Chinese Patent Application No. 201980034543, mailed on Jan. 24, 2022, 17 pages (9 pages of English Translation and 8 pages of Original Document).

Office Action received for Chinese Patent Application No. 201980036811, mailed on Feb. 8, 2022, 22 pages (12 pages of English Translation and 10 pages of Original Document).

Office Action received for Chinese Patent Application No. 201980036811, mailed on Feb. 9, 2023, 7 pages (4 pages of English Translation and 3 pages of Original Document).

Office Action received for Chinese Patent Application No. 202080067342, mailed on Feb. 15, 2023, 19 pages (9 pages of English Translation and 10 pages of Original Document).

Office Action received for Chinese Patent Application No. 202080067342.9, mailed on Jan. 4, 2024, 6 pages.

Office Action received for Chinese Patent Application No. 202080067342.9, mailed on Sep. 20, 2023, 17 pages. (10 pages of English Translation and 7 pages of Original Document).

Office Action received for Chinese Patent Application No. 202080067396.5, mailed on Mar. 7, 2024, 22 pages. (14 pages of English Translation and 8 pages of Original Document).

Office Action received for Chinese Patent Application No. 202080068829.9, mailed on Jul. 17, 2024, 08 pages.

Office Action received for Chinese Patent Application No. 202080068829.9, mailed on Apr. 7, 2023, 18 pages (12 pages of English Translation and 6 pages of Original Document).

Office Action received for Chinese Patent Application No. 202080068829.9, mailed on Apr. 22, 2024, 18 pages. (11 pages of English Translation and 7 pages of Original Document).

Office Action received for Chinese Patent Application No. 202080068829.9, mailed on Nov. 10, 2023, 17 pages (10 pages of English Translation and 7 pages of Original Document).

Office Action received for Chinese Patent Application No. 202080068856.6, mailed on Nov. 9, 2023, 15 pages. (9 pages of English Translation and 6 pages of Original Document).

Office Action received for Chinese Patent Application No. 202080068856.6, mailed on Apr. 6, 2023, 16 pages. (11 pages of English Translation and 5 pages of Original Document).

Office Action received for Chinese Patent Application No. 202080068856.6, mailed on Apr. 23, 2024, 16 pages. (10 pages of English Translation and 6 pages of Original Document).

Office Action received for Chinese Patent Application No. 202080069164.3, mailed on Apr. 6, 2023, 18 pages. (12 pages of English Translation and 6 pages of Original Document).

Office Action received for Chinese Patent Application No. 202080069164.3, mailed on Jan. 4, 2024, 6 pages.

Office Action received for Chinese Patent Application No. 202080069164.3, mailed on Nov. 9, 2023, 18 pages. (11 pages of English Translation and 7 pages of Original Document).

Office Action received for Chinese Patent Application No. 202080070202.7, mailed on Sep. 20, 2023, 20 pages. (13 pages of English Translation and 7 pages of Original Document).

Office Action received for Chinese Patent Application No. 202080078792.8, mailed on Mar. 25, 2023, 29 pages. (18 pages of English Translation and 11 pages of Original Document).

Office Action received for Chinese Patent Application No. 202080078792.8, mailed on Mar. 30, 2024, 16 pages.

Office Action received for Chinese Patent Application No. 202080078792.8, mailed on Oct. 12, 2023, 25 pages. (16 pages of English Translation and 9 pages of Original Document).

Office Action received for Chinese Patent Application No. 202080084115.7, mailed on Nov. 9, 2023, 21 pages. (13 pages of English Translation and 8 pages of Original Document).

Office Action received for Chinese Patent Application No. 202180068289.9, mailed on Febuary 26, 2025, 18 pages. (11 pages of English Translation and 7 pages of Original Document).

Office Action received for Chinese Patent Application No. 202180068289.9, mailed on Jun. 28, 2024, 21 pages. (14 pages of English Translation and 7 pages of Original Document).

Office Action received for European European Application No. 19725314, mailed on Oct. 28, 2022, 3 pages.

Office Action received for European Application No. 20780176, mailed on Mar. 10, 2023, 8 pages.

Office Action received for European Application No. 20816477, mailed on May 19, 2025, 4 pages.

Office Action received for European Application No. 22705044.0, mailed on Nov. 12, 2024, 7 pages.

Office Action received for European Patent Application No. 20780175, mailed on Apr. 22, 2025, 3 pages.

Office Action received for Japanese Patent Application No. 2020-566667, mailed on Apr. 26, 2023, 8 pages (4 pages of English Translation and 4 pages of Original Document).

Office Action received for Japanese Patent Application No. 2022-520208, mailed on Aug. 7, 2024, 07 pages (03 pages of English Translation and 04 pages of Original Document).

Office Action received for Japanese Patent Application No. 2022-520209, mailed on Oct. 11, 2024, 10 pages (05 pages of English Translation and 05 pages of Original Document).

Office Action received for Japanese Patent Application No. 2022-520210, mailed on Oct. 11, 2024, 09 pages (04 pages of English Translation and 05 pages of Original Document).

Office Action received for Japanese Patent Application No. 2022-520211, mailed on Sep. 30, 2024, 06 pages (03 pages of English Translation and 03 pages of Original Document).

Office Action received for Japanese Patent Application No. 2022-526352, mailed on Dec. 11, 2024, 06 pages (03 pages of English Translation and 03 pages of Original Document).

Office Action received for Japanese Patent Application No. 2022-533388, mailed on Jan. 29, 2025, 08 pages (04 pages of English Translation and 04 pages of Original Document).

Office Action with English translation only, mailed on Jul. 18, 2024, by the China National Intellectual Property Administration for Chinese Application No. 2020800688566, 7 pages.

Request for the Submission of an Opinion received for Korean Patent Application No. 10-2022-7012146, mailed on Mar. 4, 2025, 08 pages (4 pages of English Translation and 4 pages of Original Document).

Request for the Submission of an Opinion received for Korean Patent Application No. 10-2020-7037585, mailed on May 1, 2024, 08 pages (4 pages of English Translation and 4 pages of Original Document).

Communication dated Mar. 25, 2021 and Search Report dated Mar. 17, 2021 issued in corresponding European Patent Application No. 20201822.2. (7 pages).

European Search Report issued in corresponding Application No. EP 19 21 3432 dated May 8, 2020.

European Search Report issued in corresponding Application No. EP 20 20 1817 dated Mar. 17, 2021.

Extended European Search Report dated Mar. 25, 2021, issued by the European Patent Office in corresponding European Application No. 20201816.4. (8 pages).

Extended European Search Report mailed on Jul. 8, 2021, by the European Patent Office for European Application No. (2115595534).

International Preliminary Report on Patentability received for PCT Patent Application No. PCT/EP2020/084408, mailed on Jun. 16, 2022, 8 pages.

(56)　　　　References Cited

OTHER PUBLICATIONS

International Preliminary Report on Patentability received for PCT Patent Application No. PCT/EP2021/078142, mailed on Apr. 27, 2023, 8 pages.
International Preliminary Report on Patentability received for PCT Patent Application No. PCT/EP2021/078304, mailed on Apr. 27, 2023, 8 pages.
International Preliminary Report on Patentability received for PCT Patent Application No. PCT/EP2022/051090, mailed on Aug. 10, 2023, 11 pages.
International Preliminary Report on Patentability received for PCT Patent Application No. PCT/EP2022/053062, mailed on Aug. 24, 2023, 11 pages.
International Search Report and Written Opinion received for PCT Patent Application No. PCT/EP2020/084408, mailed on Feb. 12, 2021, 11 pages.
International Search Report and Written Opinion received for PCT Patent Application No. PCT/EP2021/078142, mailed on Jan. 4, 2022, 11 pages.
International Search Report and Written Opinion received for PCT Patent Application No. PCT/EP2022/051090, mailed on May 10, 2022, 14 pages.
International Search Report and Written Opinion received for PCT Patent Application No. PCT/EP2022/053062, mailed on May 12, 2022, 13 pages.
International Search Report and Written Opinion received for PCT Patent Application No. PCT/EP21/078304, mailed on Dec. 23, 2021, 11 pages.
Office Action received for European Application No. 20816477, mailed on Aug. 16, 2023, 6 pages.
Wu et al., "Methanation of CO2 and reverse water gas shift reaction on Ni/Si0 2 catalysts: the influence of particle size on selectivity and reaction pathway", Catalysis Science & Technology. vol. 5, No. 8, Jan. 1, 2015, pp. 4154-4163.
Yabe, Tomohiro et al., "Low-temperature dry reforming of methane to produce syngas in an electric field over La-doped Ni/ZrO2 catalysts", Fuel Processing Technology, Dec. 23, 2016, vol. 158, pp. 96-103, Elsevier B.V., NL. (8 pages).
U.S. Appl. No. 17/637,539, Peter Mølgaard Mortensen, filed Feb. 23, 2022.
U.S. Appl. No. 18/990,223, Peter Mølgaard Mortensen, filed Dec. 20, 2024.
U.S. Appl. No. 17/778,039, Peter Mølgaard Mortensen, filed May 19, 2022.
U.S. Appl. No. 18/245,730, Sudip De Sarkar, filed Mar. 17, 2023.
U.S. Appl. No. 18/026,977, Kim Aasberg-Petersen, filed Mar. 17, 2023.
U.S. Appl. No. 18/276,341, Ole Frej Alkilde, filed Aug. 8, 2023.
First Office Action with English translation, issued on May 26, 2025 by the China National Intellectual Property Administration in related Chinese Application No. 2022800093460, 19 pages.
U.S. Appl. No. 18/965,188, Sudip De Sarkar, filed Dec. 2, 2024.
U.S. Appl. No. 17/420,491, Sudip De Sarkar, filed Jul. 2, 2021.
Request for the Submission of an Opinion received for Korean Patent Application No. 10-2020-7037588, mailed on May 1, 2024, 8 pages (4 pages of English Translation and 4 pages of Original Document).
Search Report mailed on Jan. 28, 2019, by the Danish Patent Office for Application No. PA 2018 00249.
Second Office Action received for Chinese Patent Application No. 201980034543, mailed on Aug. 16, 2022, 17 pages (10 pages of English Translation and 7 pages of Original Document).
Technology for Application of Industrial Control Computers, pp. 303-304, Beijing: Chemical Engineering Press, May 1982.
Wang, Y., et al., "High temperature solid oxide H2O/Co2 co-electrolysis for syngas production", Fuel Processing Technology, Nov. 14, 2016, vol. 161, pp. 248-258. (12 pages).
Wismann, Sebastian T., et al., "Electrified methane reforming: A compact approach to greener industrial hydrogen production,"

Science, May 24, 2019, p. 756-759, vol. 364, American Association for the Advancement of Science, Washington, D.C.
Written Decision on Registration received for Korean Patent Application No. 10-2020-7037585, mailed on Feb. 19, 2025, 5 pages (3 pages of English Translation and 2 pages of Original Document).
Written Decision on Registration received for Korean Patent Application No. 10-2020-7037588, mailed on Feb. 19, 2025, 5 pages (3 pages of English Translation and 2 pages of Original Document).
Written Opinion (PCT/ISA/237) mailed on Oct. 8, 2018, by the European Patent Office as the International Searching Authority for International Application No. PCT/EP2018/059657. (8 pages).
Xu, "Methane steam reforming, methanation and water-gas shift: I. intrinsic kinetics", American Institution of Chemical Engineers Journal, vol. 35, No. 1, Jan. 1989, pp. 88-96.
Zhou et al. "Investigation of a novel porous anodic alumina plate for methane steam reforming: Hydrothermal stability, electrical heating possibility and reforming reactivity", GB, vol. 34, No. 2, Jan. 1, 2009, p. 844-858.
Aasberg-Petersen , et al., "Chapter 4—Synthesis gas production for FT synthesis", Studies in Surface Science and Cataiysis, vol. 152, 2004, pp. 258-405.
Ali Shahid et al: "Modeling a novel combined solid oxide electrolysis cell (SOEC)—Biomass gasification renewable methanol production system", Renewable Energy, Pergamon Press, Oxford, GB, vol. 154, Dec. 27, 2019, pp. 1025-1034, XP086126465.
Banis, L.J. and H.H. Hausner, Fundamental Phenomena in the Material Sciences, vol. 1: Sintering and Plastic Deformation, pp. v-101, 1964 (Year: 1964.
Boccuzzi et al., "FTIR study of methanol decomposition on gold catalyst for fuel Cells", Journal of Power Sources, vol. 118, No. 1-2, May 25, 2003, pp. 304-310.
Communication about intention to grant a European patent received for European Application No. 19723134, mailed on Feb. 16, 2022, 6 pages.
Communication about intention to grant a European patent received for European Application No. 19723428, mailed on Dec. 12, 2022, 6 pages.
Communication dated May 27, 2021 and European Search Report dated May 18, 2021 issued by the European Patent Office in corresponding European Application No. 20216621.1. (8 pages).
Danish Search Report dated Mar. 27, 2020 issued by the Danish Patent and Trademark Office in Danish Patent Application No. PA 201901437. (9 pages).
Danish Search Report for Danish Application No. PA 2019 01145 dated Mar. 12, 2020 (7 pages).
Danish Search Report for Danish Application No. PA 2019 01432 dated Mar. 27, 2020 (10 pages).
Danish Search Report issued in corresponding Danish Patent Application No. PA201901433 dated Apr. 15, 2020. (9 pages).
Danish Search Report issued in corresponding Danish Patent Application No. PA201901435 dated Apr. 24, 2020. (9 pages).
Danish Search Report issued in corresponding Patent Application No. PA 2019 01324 dated May 27, 2020, 8 pages.
Danish Search Report issued in corresponding Patent Application No. PA 2019 01434 dated May 27, 2020 (8 pages).
Danish Search Report mailed on Dec. 1, 2022 by the Danish Patent and Trademark Office for Danish Application No. PA 2022 00442, 8 Pages.
Danish Search Report mailed on Nov. 17, 2022 by the Danish Patent and Trademark Office for Danish Application No. PA 2022 00444, 9 Pages.
Decision to grant a European patent received for European Application No. 19723134, mailed on Jun. 17, 2022, 2 pages.
Decision to grant a European patent received for European Application No. 19723428, mailed on Jun. 9, 2023, 3 pages.
Decision to Grant a Patent received for Japanese Patent Application No. 2020-566667, mailed on Dec. 6, 2023, 5 pages (2 pages of English Translation and 3 pages of Original Document).
Decision to Grant a Patent received for Japanese Patent Application No. 2022-520208, mailed on Jan. 8, 2025, 05 pages (02 pages of English Translation and 03 pages of Original Document).

(56) References Cited

OTHER PUBLICATIONS

Decision to Grant a Patent received for Japanese Patent Application No. 2022-520209, mailed on Mar. 12, 2025, 05 pages (02 pages of English Translation and 03 pages of Original Document).

Decision to Grant a Patent received for Japanese Patent Application No. 2022-520211, mailed on Feb. 5, 2025, 05 pages (02 pages of English Translation and 03 pages of Original Document).

Decision to Grant a Patent received for Japanese Patent Application No. 2022-526352, mailed on Mar. 26, 2025, 05 pages (02 pages of English Translation and 03 pages of Original Document).

Decision to grant received for European Application No. 20780176, mailed on Jun. 15, 2023, 2 pages.

European Search Report and Search Opinion Received for EP Application No. 20216623, mailed on Jun. 7, 2021, 7 pages.

European Search Report and Search Opinion received for European Application No. 18175366, mailed on Nov. 7, 2018, 7 pages.

European Search Report for European Application No. 20 21 6617 dated May 10, 2021. (9 pages).

First Office Action with English translation mailed on September 3. 2023, by the Saudi Authority for Intellectual Property for Saudi Arabian Application No. 522432548, 19 pages.

International Preliminary Report on Patentability received for PCT Patent Application No. PCT/EP20/076695, mailed on Apr. 14, 2022, 9 pages.

International Preliminary Report on Patentability received for PCT Patent Application No. PCT/EP20/076698, mailed on Apr. 14, 2022, 8 pages.

International Preliminary Report on Patentability received for PCT Patent Application No. PCT/EP2019/062420, mailed on Dec. 10, 2020, 8 pages.

International Preliminary Report on Patentability received for PCT Patent Application No. PCT/EP2019/062423, mailed on Dec. 10, 2020, 8 pages.

International Preliminary Report on Patentability received for PCT Patent Application No. PCT/EP2019/062424, mailed on Dec. 10, 2020, 8 pages.

International Preliminary Report on Patentability received for PCT Patent Application No. PCT/EP2020/076700, mailed on Apr. 14, 2022, 9 pages.

International Preliminary Report on Patentability received for PCT Patent Application No. PCT/EP2020/076707, mailed on Apr. 14, 2022, 9 pages.

International Preliminary Report on Patentability received for PCT Patent Application No. PCT/EP2020/076713, mailed on Apr. 14, 2022, 8 pages.

International Preliminary Report on Patentability received for PCT Patent Application No. PCT/EP2020/081700, mailed on May 27, 2022, 14 pages.

International Preliminary Report on Patentability received for PCT Patent Application No. PCT/EP2021/086999, mailed on Jul. 6, 2023, 12 pages.

International Preliminary Report on Patentability received for PCT Patent Application No. PCT/EP220/076704, mailed on Apr. 14, 2022, 8 pages.

International Search Report (PCT/ISA/210) and Written Opinion (PCT/ISA/237) mailed on Feb. 23, 2021, by the European Patent Office as the International Searching Authority for International Application No. PCT/EP2020/081700. (20 Pages).

International Search Report (PCT/ISA/210) mailed on Oct. 8, 2018, by the European Patent Office as the International Searching Authority for International Application No. PCT/EP2018/059657. (6 pages).

International Search Report and Written Opinion received for PCT Patent Application No. PCT/EP2019/062420, mailed on Jul. 23, 2019, 10 pages.

International Search Report and Written Opinion received for PCT Patent Application No. PCT/EP2019/062423, mailed on Aug. 26, 2019, 10 pages.

International Search Report and Written Opinion received for PCT Patent Application No. PCT/EP2019/062424, mailed on Jul. 26, 2019, 11 pages.

International Search Report and Written Opinion received for PCT Patent Application No. PCT/EP2020/076695, mailed on Nov. 23, 2020, 11 pages.

International Search Report and Written Opinion received for PCT Patent Application No. PCT/EP2020/076698, mailed on Nov. 26, 2020, 9 pages.

International Search Report and Written Opinion received for PCT Patent Application No. PCT/EP2020/076700, mailed on Nov. 26, 2020, 11 pages.

International Search Report and Written Opinion received for PCT Patent Application No. PCT/EP2020/076704, mailed on Nov. 26, 2020, 11 pages.

International Search Report and Written Opinion received for PCT Patent Application No. PCT/EP2020/076707, mailed on Nov. 27, 2020, 11 pages.

International Search Report and Written Opinion received for PCT Patent Application No. PCT/EP2020/076713, mailed on Nov. 26, 2020, 11 pages.

CN Office Action, including Search Report received for Chinese Patent Application No. 202080017669, mailed on Aug. 4, 2023, 12 pages (6 pages of English Translation and 6 pages of Original Document).

Danish Search Report mailed on Sep. 30, 2019 by the Danish Patent and Trademark Office for Danish Patent Application No. PA 2019 00434. (9 pages).

Decision to Grant received for Japanese Patent Application No. 2022-533388, mailed on Aug. 27, 2025, 5 pages (2 pages of English Translation and 3 pages of Original Document).

International Preliminary Report on Patentability received for PCT Patent Application No. PCT/EP20/059598, mailed on Oct. 21, 2021, 9 pages.

International Preliminary Report on Patentability received for PCT Patent Application No. PCT/EP20/059872, mailed on Oct. 7, 2021, 8 pages.

International Search Report and Written Opinion received for PCT Patent Application No. PCT/EP2020/059598, mailed on Jul. 15, 2020, 11 pages.

International Search Report and Written Opinion received for PCT Patent Application No. PCT/EP2020/059872, mailed on Jul. 10, 2020, 10 pages.

Office Action received for Chinese Patent Application No. 202080017634, mailed on Aug. 11, 2023, 15 pages (8 pages of English Translation and 7 pages of Original Document).

Office Action received for Chinese Patent Application No. 202080017634, mailed on Mar. 13, 2024, 15 pages (9 pages of English Translation and 6 pages of Original Document).

Office Action received for Chinese Patent Application No. 202080017634, mailed on Sep. 20, 2024, 8 pages of Original document only.

Office Action received for Chinese Patent Application No. 202080017669, mailed on Feb. 8, 2024, 10 pages (6 pages of English Translation and 4 pages of Original Document).

Office Action received for Chinese Patent Application No. 202280009346.0, mailed on May 26, 2025, 24 pages (12 pages of original office action and 12 pages of English Translation).

Office Action received for European Application No. 20717613, mailed on Mar. 27, 2024, 4 pages.

Office Action received for European Application No. 20717645, mailed on Apr. 25, 2024, 3 pages.

Office Action received for European Application No. 21783568.5, mailed on Dec. 3, 2025, 3 pages.

Office Action received for Korean Patent Application No. 10-2021-7026351, mailed on Apr. 7, 2025, 25 pages (14 pages of English Translation and 11 pages of Original Document).

Office Action received for Korean Patent Application No. 10-2021-7026711, mailed on Apr. 11, 2025, 16 pages (9 pages of English Translation and 7 pages of Original Document).

Office Action received for Korean Patent Application No. 10-2022-7013630, mailed on Jul. 8, 2025, 8 pages (4 pages of original office action and 4 pages of English Translation).

Office Action received for Korean Patent Application No. 10-2022-7018777, mailed on Dec. 10, 2025, 22 pages (10 pages of original office action and 12 pages of English Translation).

SYNTHESIS GAS PRODUCTION FROM CO$_2$ AND STEAM FOR SYNTHESIS OF FUELS

TECHNICAL FIELD

The present invention relates to a system for providing a hydrocarbon product stream. The system comprises, a Fischer-Tropsch (F-T) section, an electrolysis section arranged upstream said F-T section, a first feed comprising CO$_2$ to the electrolysis section, a second feed comprising H$_2$O to the electrolysis section, and a first electrical steam reformer section. A process is also provided for converting a first feed comprising CO$_2$ and a second feed comprising H$_2$O to a first hydrocarbon product stream using the system according to the invention. The system can be combined with an upgrading section, in a gas-to-liquid (GTL) plant.

BACKGROUND

A Gas-to-Liquids (GTL) plant for production of synthetic hydrocarbons or fuels (such as diesel, kerosene, jet fuel, naphtha) from for example natural gas typically comprises three main sections:
1) Synthesis Gas Production
2) Production of raw product of hydrocarbons by the Fischer-Tropsch synthesis
3) Upgrading of the raw product to the end product(s)

Synthesis gas for production of hydrocarbons by the Fischer-Tropsch synthesis is a mixture of mainly carbon monoxide and hydrogen. The synthesis gas may also comprise other components such as CO$_2$, steam, nitrogen, and methane normally in minor amounts. Synthesis gas production is today often carried out by Autothermal Reforming (ATR) with natural gas or similar hydrocarbon-containing feedstock. Oxygen for the ATR is typically supplied from an air separation unit (ASU). This process can be performed with fairly high carbon and energy efficiency. However, part of the feed will unavoidably be converted into carbon dioxide leading to negative impact on the climate.

Significant progress is being made to develop and optimize technologies for production of power from renewable sources (e.g. wind, solar). However, it is expected that for heavy duty traffic and for aviation, fuels based on hydrocarbons will be needed for many years to come.

In a GTL plant based on natural gas with ATR, part of the F-T tail gas can be recycled to the ATR. This is done both to adjust the desired Hz/CO-ratio of the synthesis gas and to increase the carbon efficiency of the GTL plant. However, in a plant with CO$_2$ and H$_2$O as feed and synthesis gas production by electrolysis, tail gas recycle to the electrolysis units is not feasible. Addition of the tail gas to an SOEC unit could lead to carbon formation in the SOEC electrolysis unit. Tail gas cannot be converted into synthesis gas in low temperature electrolysis units. Hence, there is a need to find a process for utilizing the tail gas to maximise the plant carbon (and energy) efficiency.

One way would be to direct the tail gas to a steam reformer for additional production of synthesis gas. However, steam reforming is an endothermic reaction and requires a significant amount of combustion in a furnace to provide the required energy. This combustion will lead to additional carbon dioxide emissions and reduce the overall carbon efficiency. Furthermore, the fuel required for the combustion will originally be produced from electrolysis utilizing electrical power. This substantially increases the power consumption of the plant.

Hence, it is desirable to develop a technology for production of synthetic hydrocarbons such as diesel and jet fuel, which uses CO$_2$ as the primary carbon-containing feedstock and utilizing renewable power. This could reduce the climate impact compared to the technology used today. Ideally, such a technology should convert a high fraction of the carbon dioxide in the feed as possible into desired end products such as diesel and kerosene.

Related technology is described in applicant's co-pending application EP20216617.9.

SUMMARY

It has now surprisingly been found that utilization of an electrical steam reformer for converting the tail gas from an FT-section into synthesis gas reduces the overall power requirements for synthesis gas production and/or reduces the CO$_2$ emissions in a GTL plant.

This is surprising as such an electrical steam reformer itself utilizes electrical power.

So, in a first aspect the present invention relates to a system for providing a first hydrocarbon product stream, said system comprising:
- a Fischer-Tropsch (F-T) section,
- an electrolysis section arranged upstream said F-T section,
- a first feed comprising CO$_2$ to the electrolysis section,
- a second feed comprising H$_2$O to the electrolysis section,
- a first electrical steam reformer section,
- wherein
- said electrolysis section is arranged to provide a first syngas stream from said first and said second feeds,
- said F-T section is arranged to receive at least at least a first portion of said first syngas stream and convert it to a first hydrocarbon product stream and a tail gas stream,
- and wherein—optionally—said first electrical steam reformer section is arranged to receive at least a second portion of said first syngas stream and convert it to a second syngas stream,
- said first electrical steam reformer section is arranged to receive at least a first portion of said tail gas stream and convert it to a second syngas stream, and wherein said second syngas stream is arranged to be fed to the F-T section, preferably in admixture with the first syngas stream.

In a further aspect, the invention provides a GTL plant comprising the system as described herein, said GTL plant further comprising an upgrading section arranged to receive the first hydrocarbon product stream and provide an end product stream.

A process is also provided for converting a first feed comprising CO$_2$ and a second feed comprising H$_2$O to a first hydrocarbon product stream in a system according to the invention.

Further aspects and details of the invention are provided in the following description text, as well as the appended claims and figures.

LEGENDS

Figure 2:
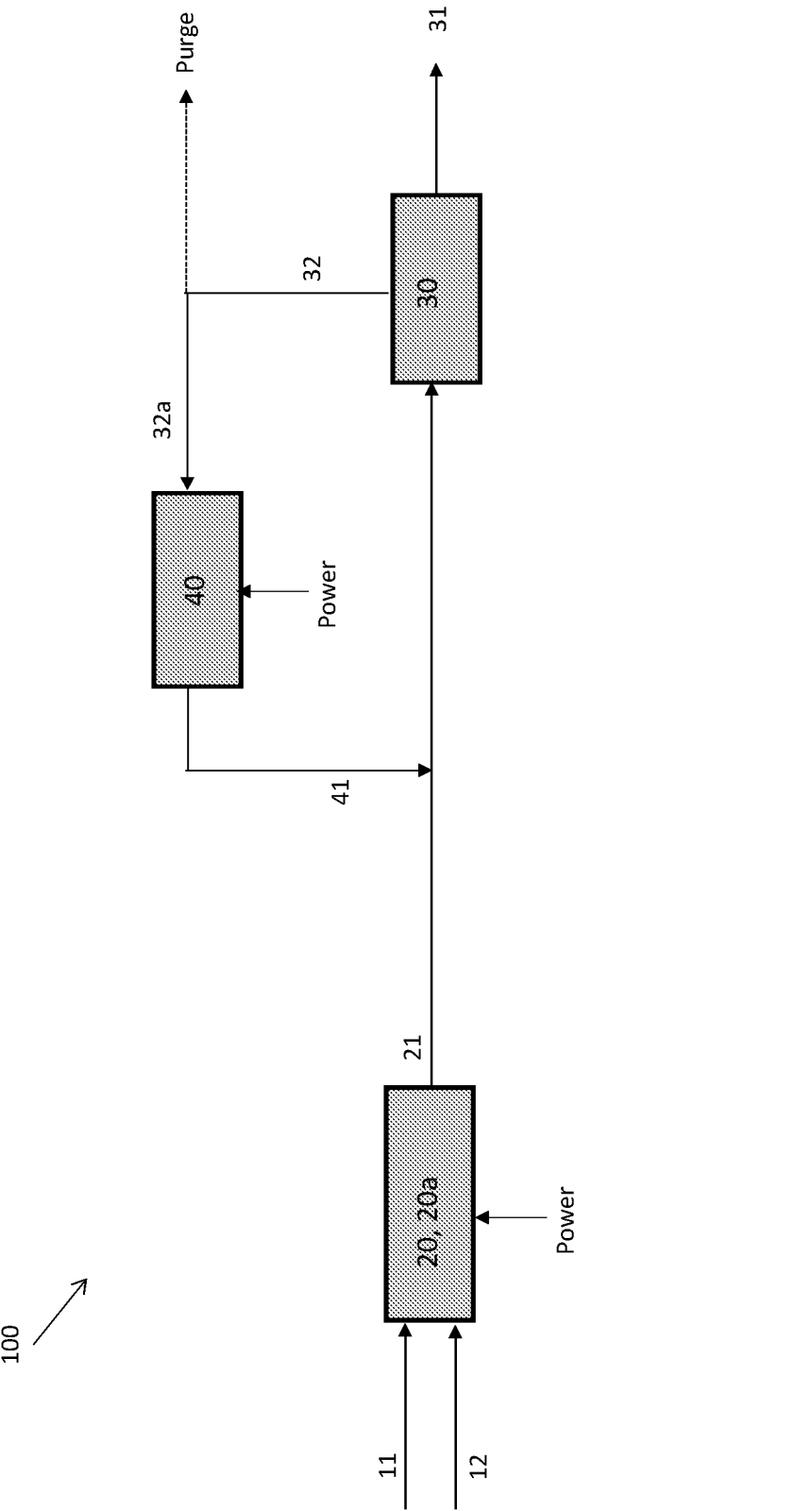

FIGS. 1-2 illustrate schematic layouts of various embodiments of a system according to the invention

DETAILED DISCLOSURE

Unless otherwise specified, any given percentages for gas content are % by volume.

The term "synthesis gas" is used interchangeably with the term "syngas" and is meant to denote a gas comprising hydrogen, carbon monoxide and also carbon dioxide and small amounts of other gasses, such as argon, nitrogen, methane, steam, etc.

SPECIFIC EMBODIMENTS

The invention describes a system for providing a first hydrocarbon product stream In general terms, the system comprises:

a Fischer-Tropsch (F-T) section, an electrolysis section arranged upstream said F-T section, a first feed comprising $CO_2$ to the electrolysis section, a second feed comprising $H_2O$ to the electrolysis section, a first electrical steam reformer section.

These components of the system, and their relationship, will be described in the following.

First Feed Comprising $CO_2$

A first feed comprising carbon dioxide is provided to the electrolysis section. Suitably, the first feed consists essentially of $CO_2$. The first feed of $CO_2$ is suitably "$CO_2$ rich" meaning that the major portion of this feed is $CO_2$; i.e. over 75%, such as over 85%, preferably over 90%, more preferably over 95%, even more preferably over 99% of this feed is $CO_2$. One source of the first feed of carbon dioxide can be one or more exhaust stream(s) from one or more chemical plant(s). One source of the first feed of carbon dioxide can also be carbon dioxide captured from one or more process stream(s) or atmospheric air. Another source of the first feed could be $CO_2$ captured or recovered from the flue gas for example from fired heaters, steam reformers, and/or power plants. The first feed may in addition to $CO_2$ comprise for example steam, oxygen, nitrogen, oxygenates, amines, ammonia, carbon monoxide, and/or hydrocarbons.

In one aspect, the first feed comprises a minor amount of hydrocarbons (typically methane), preferably in an amount of less than 10%, such as less than 5%, or most preferably less than 3% by volume of said first feed.

Prior to being provided to the electrolysis section, the first feed comprising carbon dioxide may be passed through a $CO_2$-cleaning unit for removing impurities, such as Cl (e.g. HCl), sulfur (e.g. $SO_2$, $H_2S$, COS), Si (e.g. siloxanes) and/or As. This ensures the protection of downstream units, in particular the subsequent electrolysis section.

Second Feed Comprising $H_2O$

A second feed comprising water (for example in the form of steam) is provided to the electrolysis section. Suitably, the second feed consists essentially of $H_2O$. The second feed of $H_2O$ is suitably "$H_2O$ rich" meaning that the major portion of this feed is $H_2O$; i.e. over 75%, such as over 85%, preferably over 90%, more preferably over 95%, even more preferably over 99% of this feed is $H_2O$.

One source of the second feed of $H_2O$ is process steam, which is generally available in industrial plants. The second feed of $H_2O$ may also be obtained from other units, reactors or sections in the system or plant of the current invention. In one embodiment the steam is provided from a waste heat boiler used for cooling the effluent stream from the electrical reforming reactor.

In addition to $H_2O$, the second feed may for example comprise nitrogen, argon, carbon dioxide, hydrogen, and/or hydrocarbons, in minor amounts.

Third Feed Comprising $CO_2$

Optionally, a third feed comprising $CO_2$ may be provided to the first electrical steam reformer section in the system described above. Suitably, the third feed consists essentially of $CO_2$. All details relating to the first feed comprising $CO_2$ (above) apply equally to the third feed comprising $CO_2$. In one preferred system, a single feed comprising $CO_2$ is supplied to the system and arranged to be split into first and third feeds comprising $CO_2$. It is advantageously to feed $CO_2$ to the electrical steam reformer section as this allows for utilizing the typical high temperatures of this section for CO production from the $CO_2$.

In an embodiment, the third feed is a part of the effluent of said electrolysis section and will consequently comprise CO and $CO_2$. In this configuration, unconverted $CO_2$ from the electrolysis section can be converted into CO in a higher yield in the electrical steam reformer section. This stream may be provided from e.g. the first electrolysis unit or the single electrolysis unit.

In another embodiment, the third feed may comprise $H_2$, and is suitably part of the effluent of said electrolysis section. This stream may be provided from e.g. the second electrolysis unit or the single electrolysis unit. $H_2$ can be an advantageous to have as a co-feed when used as a reactant for the $CO_2$ reverse water gas shift reaction according to the reaction scheme. Additionally, $H_2$ serves to reduce the risk of carbon formation, which is typically associated with CO production.

Electrolysis Section

An electrolysis section is arranged to provide a first synthesis gas (syngas) stream from the first and said second feeds.

The electrolysis section may comprise one, or a plurality of electrolysis units. A single electrolysis unit can comprise a plurality of electrolysis stacks with associated equipment. The electrolysis section may additionally comprise compressor units and/or mixer units as required.

Electrolysis of steam and $CO_2$ proceeds via reactions (1) and (2):

$$H_2O \longrightarrow H_2 + 1/2\,O_2 \tag{1}$$

$$CO_2 \longrightarrow CO + 1/2\,O_2 \tag{2}$$

The electrolysis products of reactions (1) and (2) are $H_2$ and CO; i.e. the primary constituents of a synthesis gas.

In some cases, it is not possible to convert all of the $CO_2$ and/or $H_2O$ in the electrolysis unit or units. Separation of the product stream(s) may occur downstream the electrolysis unit(s) followed by recycle of part or all of the unconverted $CO_2$ and/or steam to the inlet of the electrolysis unit(s).

In some cases (with or without recycle) the non-converted $CO_2$ is contained in the first synthesis gas. Most of the non-converted $H_2O$ will typically be condensed downstream the electrolysis units leaving only a small amount of $H_2O$ in the first synthesis gas (normally less than 5%, preferably less than 2%).

Both of the above reactions require electrical power to proceed in an electrolysis unit. The electrolysis section therefore includes a supply of electrical power, which is preferably at least partly a renewable supply, such as wind and solar energy.

Reaction (1) may proceed either in a low temperature electrolysis unit such as alkaline electrolysis (AEL) or polymer electrolyte electrolysis (PEM). Reaction (1) may also take place in a high temperature electrolysis unit such as a Solid Oxide Electrolysis (SOE) Unit. Reaction (2) may also take place in an SOE unit.

Reaction (1) and (2) may take place in separate electrolysis units with separate feeds comprising steam and $CO_2$, respectively. In this case the effluent streams from the steam electrolysis unit and the $CO_2$ electrolysis unit are combined to produce a synthesis gas stream. In this aspect, therefore, the electrolysis section comprises at least a first electrolysis unit and a second electrolysis unit, wherein the first electrolysis unit is arranged to convert the first feed comprising $CO_2$ to a first stream comprising CO, and wherein the second electrolysis unit is arranged to convert the second feed comprising $H_2O$ to a second stream comprising $H_2$, and wherein said electrolysis section is further arranged to combine said first stream comprising CO with said second stream comprising $H_2$ to said first syngas stream.

Another possibility is that both reactions (1) and (2) take place in the same electrolysis unit with a feed comprising both steam and $CO_2$. Thus, in the system according to the invention, the electrolysis section may comprise a single electrolysis unit arranged to convert said first and said second feeds to a first syngas stream, preferably wherein first and said second feeds are arranged to be mixed prior to being fed to the electrolysis section. In other words, the first and second feeds are converted in this same "single" electrolysis unit. In this case various other reactions may also occur:

$$CO + H_2O \longrightarrow CO_2 + H_2 \qquad (3)$$

$$3H_2 + CO \longrightarrow CH_4 + H_2O \qquad (4)$$

Regardless of which type of electrolysis unit used, it is usually not possible to achieve complete conversion of neither steam nor $CO_2$. Specifically, for $CO_2$ conversion, the risk of carbon formation typically sets a confined limit for how high conversion can be achieved as otherwise the Boudouard reaction may take place according to the reaction:

$$2CO \longrightarrow C + CO_2 \qquad (5)$$

In the case where a single electrolysis unit is used for both $H_2O$ and $CO_2$ electrolysis, also the CO decomposition reactions gives a confinement in allowable conversion to CO according to the reaction:

$$CO + H_2 \longrightarrow C + H_2O \qquad (6)$$

Carbon formation is an undesired side reaction.

In this case, the methane (and any other hydrocarbon) produced in reaction (4) passes directly through the F-T section, and can comprise a portion of the hydrocarbon outletted from the F-T section in the tail gas. This hydrocarbon is then converted in the electrical steam reformer section (described in detail below). Such an arrangement also provides improved flexibility in the system and process of the invention.

One or all of the electrolysis units in the electrolysis section may comprise a solid oxide electrolysis (SOE) unit. The second electrolysis unit (used to electrolyse the second feed of $H_2O$) may be an alkaline/polymer electrolyte membrane electrolysis unit e.g. an alkaline/PEM electrolysis unit. When the electrolysis of $H_2O$ to $H_2$ is based on liquid water, the heat of evaporation of the water is saved. SOE and alkaline/PEM electrolysis units are well known in the art, in particular alkaline/PEM electrolysis. For instance, applicant's WO 2013/131778 describes SOEC-CO2. One embodiment is a combination of SOEC-CO2 and alkaline/PEM electrolysis.

As mentioned, the electrolysis section is arranged to provide a first synthesis gas (syngas) stream from the first and said second feeds. The first syngas stream may have the following composition (by volume):

40-70% $H_2$ (dry)

10-30% CO (dry)

2-30% $CO_2$ (dry)

0.5-8% $CH_4$ preferably 0-8% $CH_4$

In one aspect, electrolysis of $CO_2$ may take place partially. The synthesis gas produced may thus have a molar ratio $CO/CO_2$ of 0.2 or higher. The electrolysis may be purposely conducted so that more CO is produced and the resulting molar ratio of CO to $CO_2$ is above such as above 0.3 or above 0.4 or 0.5, for instance 0.6 or 0.7, or 0.8 or 0.9, thereby enabling easier tailoring of the relative content of CO, $CO_2$ and $H_2$ in the resulting synthesis gas to the proper module as described below for subsequent conversion.

In one aspect, a Pressure Swing Adsorption (PSA) unit, a Temperature Swing Adsorption (TSA) unit and/or a recycle compressor-system may be present to purify the stream from $CO_2$ electrolysis. The PSA unit provides a stream rich in CO, normally above 90%, such as above 95% or even above 99% CO, as well as a stream rich in $CO_2$ which is withdrawn at low pressure and can therefore be compressed and recycled to the $CO_2$ electrolysis.

Various operations may be carried out on the first syngas stream (and the second syngas stream, or the combined first and second syngas streams) prior to it/them being fed to the F-T section.

In most cases the synthesis gas stream(s) will be cooled to below the dew point to condense out part of the water before the synthesis gas streams are routed to the F-T section. Other adjustments to the synthesis gas, such as removal of part or all of the $CO_2$ or part or all of the $H_2O$, may also take place before the synthesis gas is directed to the F-T section.

The desired $H_2/CO$ molar ratio in the combined first and second synthesis gas is called $(H_2/CO)_{Ref}$. At the inlet of the F-T section, $(H_2/CO)_{Ref}$ is typically between 1.8 and 2.2 such as between 1.9 and 2.1 or around 2.

The synthesis gas is routed from the electrolysis section to the F-T section.

Fischer-Tropsch (F-T) Section

An F-T section is arranged to receive at least a portion (i.e. a first portion) of the first syngas stream and convert it to a first (raw) hydrocarbon product stream and a tail gas stream. The hydrocarbon product stream is typically sent to an upgrading section for further refining. The composition of the raw hydrocarbon product stream from the F-T section depends on the type of catalyst, reaction temperature etc. that are used in the F-T process.

The F-T section comprises one or more F-T reactors. FT technology is well-known in the art and reference is particularly made to Steynberg A. and Dry M. "Fischer-Tropsch Technology", Studies in Surface Sciences and Catalysts, vol. 152.

This tail gas typically comprises various components such as $H_2$ (5-40%), CO (5-40%), $CO_2$ (10-70%), $CH_4$ (5-40%), as well as various other components such as $C_2$-$C_6$ paraffins and $C_2$-$C_6$ olefins in smaller amounts typically less than 5% (for each component).

Electrical Steam Reformer Section.

Tail gas from the Fischer-Tropsch section is directed to the electrical steam reformer section. A first electrical steam reformer section is therefore arranged to receive at least a first portion, and preferably more than 70%, more than 80%, more than 90% or more than 95% of, said tail gas stream and convert it to a second syngas stream.

In an optional aspect, the first electrical steam reformer section is arranged to receive at least a second portion of said first syngas stream and convert it to a second syngas stream. In other words, the first syngas stream is sent to both the F-T section and the first electrical steam reformer section. This allows for utilizing the high temperatures of the electrical steam reformer section to also convert part of unconverted $CO_2$ in the first syngas stream into CO according to the reverse water gas shift unit and steam reform prospective methane in the first syngas stream as well. This thereby reduces the amount of unreactive gases in the syngas and makes a more effective Fischer-Tropsch section.

The first electrical steam reformer section may comprise one, or a plurality of electrical steam reformers. Suitable electrical steam reformers for use in the electrical steam reformer section of the present invention are as disclosed in co-pending applications WO2019228797 and WO/2019/228798.

In an electrical steam reformer, the following reactions take place:

$$CH_4 + H_2O \longleftrightarrow 3H_2 + CO \quad \text{(7, reverse of reaction 2, above)}$$

$$CO + H_2O \longleftrightarrow H_2 + CO_2 \quad \text{(8, equal to reaction 3 above)}$$

i.e. (7) is steam methane reforming and (8) is water gas shift and the reverse reaction of (8) is reverse water gas shift.

Higher hydrocarbons (hydrocarbons with 2 or more carbon atoms) may also be present in the F-T tail gas. If so, these are also converted according to the following reaction:

$$C_nH_m + nH_2O \longrightarrow nCO + (m/2 + n)H_2 \quad (9)$$

Reaction (7) is very endothermic and requires significant energy input to reach the desired conversion. Preferably, the exit temperature from the electrical steam reformer is 850° C. or above such as 900° C. or above, such as 950° C. or even 1000° C. or above.

In some cases, it may be preferable to pretreat the tail gas before it is directed to the electrical reformer. The tail gas may comprise olefins in which case part or all of the olefins may be converted into paraffins upstream of the electrical steam reformer. This proceeds according to the following hydrogenation reaction:

$$C_nH_m + H_2 \longrightarrow C_nH_{(m+2)} \quad (10)$$

8

Therefore, the system according to the invention may further comprise a hydrogenation section arranged in the tail gas stream between the F-T section and the first electrical steam reformer section, said hydrogenation section being arranged to hydrogenate the tail gas stream.

Suitably hydrogenation sections are known to the skilled person. Hydrogenation may for example proceed in an adiabatic reactor before steam is added. A suitable catalyst may comprise copper. The hydrogenation temperature may be between 100° C. and 200° C. but other temperatures are also possible.

The tail gas also comprises CO. It may be desirable to convert part of the CO upstream the electrical steam reformer. This can for example be performed in an adiabatic water gas shift reactor according to reaction (8). Thus, the system according to the invention may further comprise a CO conversion section arranged in the tail gas stream between the F-T section and the first electrical steam reformer section, said CO conversion section arranged to perform water gas shift reaction and/or methanation on the tail gas stream. Suitably CO conversion sections—in particular, suitable adiabatic water gas shift or methanation reactors—are known to the skilled person.

If tail gas pretreatment is implemented, one preferable embodiment is to perform olefin hydrogenation followed by steam addition and water gas shift reaction. The resultant gas leaving the water gas shift reactor is then directed to the electrical reformer.

Thus, the system according to the invention may comprise both a CO conversion section and a hydrogenation section arranged in the tail gas stream between the F-T section and the first electrical steam reformer section, wherein the hydrogenation section is arranged upstream the CO conversion section.

Treatment of tail gas from an F-T reaction is described inter alia in EP1860063 and in WO2011151012.

The tail gas may also comprise higher hydrocarbons (hydrocarbons with 2 or more carbon atoms such as ethane, propane, . . . ). It may be desirable to remove or reduce the content of such higher hydrocarbons upstream the electrical reformer. This may be accomplished for example in an adiabatic prereformer. In the adiabatic prereformer, higher hydrocarbons are converted according to Reaction (9). In an adiabatic prereformer, reactions (7) and (8) (including the reverse of these reactions) will typically also take place, resulting in a gas at or close to chemical equilibrium according to these reactions. Adiabatic prereforming typically takes place with pellet type catalysts with nickel as the active material.

The electrical steam reformer section provides a second syngas stream. The composition of this second syngas stream is typically (by volume):

40-70% $H_2$ (dry)
10-30% CO (dry)
2-20% $CO_2$ (dry)
0.5-5% $CH_4$

The second syngas stream is arranged to be fed to the F-T section, preferably in admixture with the first syngas stream.

Gas-to-Liquid (GTL) Plant

The present invention also provides a GTL plant, which comprises the system as described herein and an upgrading section. The upgrading section is arranged to receive the first hydrocarbon product stream (i.e. the "raw product stream") and provide an end product stream. The end product stream is preferably a diesel stream, a kerosene stream, a Liquefied Petroleum Gas (LPG) stream, a naphtha stream, or two or more of these either separately or combined.

The raw product stream from the F-T section may be upgraded to desired end products such as kerosene, diesel, naphta, and LPG.

In some cases, only diesel, kerosene, and naphtha are desired end products. In this case LPG may be recycled to the synthesis gas generation unit. However, it is not possible to process the recycled LPG in an electrolysis unit without carbon formation. Instead steam may be added to the LPG and the LPG may be processed into additional synthesis gas for example in an electrical steam reformer section according to reaction (9). Reaction (9) will be accompanied by the methanation reaction and the water gas shift reaction (8).

Therefore, in the case where the upgrading section is arranged to provide an LPG stream, the GTL plant may further comprise a second electrical steam reformer section arranged to receive at least a portion of said LPG stream and convert it to a third synthesis gas stream. The third synthesis gas stream is arranged to be fed to the F-T section. Any LPG or naphtha formed may be added to the same electrical steam reformer as the tail gas.

In one embodiment the first electrical steam reformer section (which converts the tail gas into a second synthesis gas stream) and the second electrical steam reformer section (which converts the LPG into third synthesis gas stream) is the same electrical reformer. Accordingly the first and the second electrical steam reformer sections are comprised by a combined electrical steam reformer section, in which a combined synthesis gas stream is produced from at least a portion of said LPG stream and said at least a first portion of said tail gas stream, wherein the combined synthesis gas stream is arranged to be fed to the F-T section as said second syngas stream.

In some cases, the LPG may contain catalyst poisons such as sulfur. In this case the sulfur is removed upstream the relevant electrical steam reformer. If the LPG contains olefins, these may be converted upstream the electrical reformer according to reaction (10).

It may also be desirable to convert all or part of the higher hydrocarbons in the LPG to reduce the potential for carbon formation in the electrical reformer. In one embodiment, this may be accomplished by using an adiabatic prereformer. In the adiabatic prereformer, the higher hydrocarbons react with steam according to reaction (9). Reactions (7) and (8) will also take place in the adiabatic prereformer. Typically, the adiabatic prereformer operates at temperatures between 350° C. to 550° C. The effluent from the adiabatic prereformer is directed to the electrical reformer.

In some cases, naphtha may not be a desired end product. In this case the naphtha may be recycled back to the synthesis gas generation unit for additional synthesis gas production in a manner similar to LPG, described above.
Processes The present invention also provides a process for converting a first feed comprising $CO_2$ and a second feed comprising $H_2O$ to a first hydrocarbon product stream in a system as described herein. All details of the system described above are relevant to the process of the invention, mutatis mutandis.

The process comprises the general steps of:

converting said first and said second feeds to a first syngas stream in said electrolysis section, feeding at least a first portion of said first syngas stream to the F-T section and converting it to a first hydrocarbon product stream and a tail gas stream, optionally—feeding at least a second portion of said first syngas stream to the first electrical steam reformer section and converting it to a second syngas stream, feeding at least a portion of said tail gas stream to said first electrical steam reformer section and converting it to a second syngas stream, and feeding the second syngas stream to the F-T section, preferably in admixture with the first syngas stream.

In the process of the invention, at the inlet of the F-T section, $(H_2/CO)_{Ref}$ is typically between 1.8 and 2.2 such as between 1.9 and 2.1 or around 2.

To reduce the carbon emissions of the process, the electric power required to power the electrolysis section and/or the electrical steam reformer section, may be provided at least partly by renewable sources, such as wind and solar energy.

The present invention also describes a process for providing an end product stream (i.e. a purified product stream), such as a diesel stream, a kerosene stream, an LPG stream or a naphtha stream, said process comprising performing the process described above, followed by upgrading the first hydrocarbon product stream (in an upgrading section) and providing an end product stream by means of the upgrading section.

DETAILED DESCRIPTION OF THE FIGURES

FIG. 1 illustrates a schematic system 100 according to the invention. A first feed 11 comprising $CO_2$ (and preferably being pure $CO_2$) to the electrolysis section 20. In this embodiment, the electrolysis section 20 comprises at least a first electrolysis unit 20b and a second electrolysis unit 20c. The first electrolysis unit 20b receives the first feed 11 and is arranged to convert this first feed 11 to a first stream 24 comprising CO.

Similarly, a second feed 12 comprising $H_2O$ is fed to the electrolysis section 20, specifically to a second electrolysis unit 20c therein. The second electrolysis unit 20c receives the second feed 12 and converts it to a second stream 25 comprising $H_2$.

The first stream 24 comprising CO is combined with the second stream 25 comprising $H_2$ in e.g. a compressor unit to provide first syngas stream 21. In this embodiment, the entire first syngas stream 21 is passed to the F-T section 30, where it is converted to a first hydrocarbon product stream 31 and a tail gas stream 32.

The first hydrocarbon stream 31 is sent to an upgrading section (not illustrated in FIG. 1) for further processing.

Tail gas stream 32 is partly purged, and a portion 32a is fed to the first electrical steam reformer section 40. This first portion 32a of the tail gas stream 32 is converted to a second syngas stream 41 in the first electrical steam reformer section 40. The second syngas stream 41 is arranged to be fed to the F-T section 30, at the inlet thereof, where it can be processed to additional hydrocarbon product stream 31 and tail gas stream 32. As shown in FIG. 1, the second syngas stream 41 is preferably arranged to be fed to the F-T section 30 in admixture with the first syngas stream 21.

FIG. 2 illustrates a system similar to that of FIG. 1. In FIG. 2, the electrolysis section 20 comprises a single electrolysis unit 20a which is arranged to convert the first 11 and second 12 feeds to a first syngas stream 21. Preferably, the first 11 and second 12 feeds are arranged to be mixed prior to being fed to the electrolysis section 20, 20a.

In each of the above embodiments, electrical power, preferably from a renewable source, is provided to the electrolysis section 20 and the first electrical steam reformer section 40.

Although the invention has been described with reference to a number of aspects and embodiments, the person skilled in the art may combine elements from individual aspects while remaining within the scope of the invention as defined in the claims.

The invention claimed is:

1. A system for providing a first hydrocarbon product stream, said system comprising:
   a Fischer-Tropsch (F-T) section,
   an electrolysis section arranged upstream said F-T section,
   a first feed comprising $CO_2$ to the electrolysis section,
   a second feed comprising $H_2O$ to the electrolysis section, and
   a first electrical steam reformer section,
   wherein
   said electrolysis section is arranged to provide a first syngas stream from said first and said second feeds by electrolysis,
   said F-T section is arranged to receive at least a first portion of said first syngas stream and convert the first portion to a first hydrocarbon product stream and a tail gas stream,
   optionally, said first electrical steam reformer section is arranged to receive at least a second portion of said first syngas stream and convert the second portion to a second syngas stream,
   said first electrical steam reformer section is arranged to receive at least a first portion of said tail gas stream and convert the first portion to a second syngas stream, and
   said second syngas stream is arranged to be fed to the F-T section.

2. The system according to claim 1, wherein the electrolysis section comprises a single electrolysis unit arranged to convert said first and said second feeds to a first syngas stream.

3. The system according to claim 1, wherein the electrolysis section comprises at least a first electrolysis unit and a second electrolysis unit, wherein the first electrolysis unit is arranged to convert the first feed comprising $CO_2$ to a first stream comprising CO, and wherein the second electrolysis unit is arranged to convert the second feed comprising $H_2O$ to a second stream comprising $H_2$, and wherein said electrolysis section is further arranged to combine said first stream comprising CO with said second stream comprising $H_2$ to said first syngas stream.

4. The system according to claim 1, wherein one or all of the electrolysis units in the electrolysis section is/are a solid oxide electrolysis (SOE) unit.

5. The system according to claim 3, wherein the second electrolysis unit is an alkaline/polymer electrolyte membrane electrolysis unit.

6. The system according to claim 1, further comprising a hydrogenation section arranged in the tail gas stream between the F-T section and the first electrical steam reformer section, said hydrogenation section arranged to hydrogenate the tail gas stream.

7. The system according to claim 1, further comprising a CO conversion section arranged in the tail gas stream between the F-T section and the first electrical steam reformer section, said CO conversion section arranged to perform water gas shift reaction and/or methanation on the tail gas stream.

8. The system according to claim 1, comprising a CO conversion section and a hydrogenation section arranged in the tail gas stream between the F-T section and the first electrical steam reformer section, wherein the hydrogenation section is arranged upstream of the CO conversion section.

9. The system according to claim 1, further comprising a waste heat boiler arranged to cool the second syngas stream from the first electrical steam reformer section, and wherein steam provided from said waste heat boiler is provided as the second feed.

10. The system according to claim 1, further comprising a third feed comprising $CO_2$ to the first electrical steam reformer section,
    wherein said first electrical steam reformer section is arranged to receive the third feed and convert the $CO_2$ of the third feed into CO.

11. The system according to claim 10, wherein said third feed further comprises $H_2$.

12. A GTL plant comprising the system according to claim 1, said GTL plant further comprising an upgrading section arranged to receive the first hydrocarbon product stream and provide an end product stream.

13. The GTL plant according to claim 12, wherein the upgrading section is arranged to provide an LPG stream, and wherein said GTL plant further comprises a second electrical steam reformer section arranged to receive at least a portion of said LPG stream and convert it to a third syngas stream.

14. The GTL plant according to claim 13, wherein the first and the second electrical steam reformer sections are comprised by a combined electrical steam reformer section, in which a combined syngas stream is produced from at least a portion of said LPG stream and said at least a first portion of said tail gas stream, wherein the combined syngas stream is arranged to be fed to the F-T section as said second syngas stream.

15. A process for converting a first feed comprising $CO_2$ and a second feed comprising $H_2O$ to a first hydrocarbon product stream in a system according to claim 1, said process comprising the steps of,
    converting said first and said second feeds to a first syngas stream in said electrolysis section by electrolysis,
    feeding at least a first portion of said first syngas stream to said F-T section and converting the first portion to a first hydrocarbon product stream and a tail gas stream,
    optionally, feeding at least a second portion of said first syngas stream to the first electrical steam reformer section and converting the second portion to a second syngas stream,
    feeding at least a portion of said tail gas stream to said first electrical steam reformer section and converting the portion to a second syngas stream, and
    feeding the second syngas stream to the F-T section.

16. The process according to claim 15, wherein the first feed comprising $CO_2$ comprises a minor amount of hydrocarbons.

17. The process according to claim 15, wherein the $H_2/CO$-ratio in the second syngas stream at the inlet to the F-T section is between 1.8 and 2.2.

18. The process according to claim 15, wherein the electric power required to power the electrolysis section and/or the electrical steam reformer section, is provided at least partly by renewable sources.

19. A process for providing an end product stream, said process comprising performing the process according to claim 15, followed by upgrading the first hydrocarbon product stream and providing an end product stream by means of an upgrading section.

20. The system of claim 1, wherein the electrolysis section is configured for co-electrolysis of $CO_2$ and $H_2O$ to directly produce syngas and wherein the steam reformer is electrically heated without combustion.

* * * * *